(12) United States Patent
Dhandhusaria et al.

(10) Patent No.: US 11,517,346 B2
(45) Date of Patent: Dec. 6, 2022

(54) GEARLESS CANNULATED MOTOR ASSEMBLY AND SYSTEM FOR ROTATIONAL ATHERECTOMY

(71) Applicant: Cardiovascular Systems, Inc., St. Paul, MN (US)

(72) Inventors: Henisha A. Dhandhusaria, Lakeville, MN (US); Matthew W. Tilstra, Rogers, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 320 days.

(21) Appl. No.: 15/902,102

(22) Filed: Feb. 22, 2018

(65) Prior Publication Data

US 2018/0242998 A1 Aug. 30, 2018

Related U.S. Application Data

(60) Provisional application No. 62/463,137, filed on Feb. 24, 2017.

(51) Int. Cl.
*A61B 17/3207* (2006.01)
*A61B 17/00* (2006.01)
(Continued)

(52) U.S. Cl.
CPC .......... *A61B 17/320758* (2013.01); *A61B 2017/00398* (2013.01); *A61B 2017/00477* (2013.01);
(Continued)

(58) Field of Classification Search
CPC .......... A61B 17/320758; A61B 2017/320004; A61B 2017/00477; A61B 2017/00398;
(Continued)

(56) References Cited

U.S. PATENT DOCUMENTS

| 5,002,553 A | 3/1991 | Shiber |
| 6,022,363 A | 2/2000 | Walker et al. |

(Continued)

FOREIGN PATENT DOCUMENTS

| EP | 0387980 | 9/1990 |
| JP | H02279149 | 11/1990 |

(Continued)

OTHER PUBLICATIONS

Notification Concerning Transmittal of International Preliminary Report on Patentability and International Preliminary Report on Patentability issued in related PCT application No. PCT/US2018/19414, dated Sep. 6, 2019.

(Continued)

*Primary Examiner* — Robert A Lynch
(74) *Attorney, Agent, or Firm* — Barnes & Thornburg LLP; Jeffrey R. Stone

(57) ABSTRACT

A gearless rotational motor comprising a motor drive shaft adapted to be rotated by the gearless rotational motor, the motor drive shaft having a lumen, a proximal end extending proximally from the motor and a distal end extending distally away from the motor. The distal end adapted to connect with a torqueable flexible shaft whereby rotation of the motor drive shaft also rotates the torqueable flexible shaft.

6 Claims, 2 Drawing Sheets

(51) Int. Cl.
*A61B 17/32* (2006.01)
*A61B 17/22* (2006.01)

(52) U.S. Cl.
CPC .............. *A61B 2017/22038* (2013.01); *A61B 2017/320004* (2013.01); *A61B 2017/320733* (2013.01)

(58) Field of Classification Search
CPC ......... A61B 2017/320733; A61B 2017/22038; A61B 17/3207; A61B 2017/0046; A61B 2017/00486; A61B 2017/320032; A61B 2017/320766
See application file for complete search history.

(56) References Cited

U.S. PATENT DOCUMENTS

| | | |
|---|---|---|
| 2006/0189920 A1 | 8/2006 | Seeh |
| 2009/0264908 A1 | 10/2009 | Kallok et al. |
| 2011/0077673 A1 | 3/2011 | Grubac et al. |
| 2011/0087254 A1* | 4/2011 | Welty ................ A61B 17/3207 606/159 |
| 2012/0071907 A1 | 3/2012 | Pintor et al. |
| 2014/0148830 A1* | 5/2014 | Bowman ........ A61B 17/320758 606/159 |
| 2015/0005791 A1* | 1/2015 | Schoenle ....... A61B 17/320725 606/159 |
| 2015/0094749 A1 | 4/2015 | Ellering et al. |
| 2015/0257783 A1 | 9/2015 | Levine et al. |
| 2016/0120553 A1* | 5/2016 | Xie ..................... A61B 17/162 606/80 |

FOREIGN PATENT DOCUMENTS

| | | |
|---|---|---|
| JP | H08509639 | 10/1996 |
| JP | 2008532576 | 8/2008 |
| JP | 2012115689 | 6/2012 |
| JP | 2015042317 | 3/2015 |
| JP | 2016512719 | 5/2016 |
| WO | 94/24946 | 11/1994 |

OTHER PUBLICATIONS

International Search Report and Written Opinion, dated May 8, 2018 for PCT Application No. PCT/US2018/19414, filed Feb. 23, 2018.

Extended Search Report issued by the European Patent Office in related Application No. 18758132.7, dated Oct. 15, 2020.

* cited by examiner

GEARLESS CANNULATED MOTOR ASSEMBLY AND SYSTEM FOR ROTATIONAL ATHERECTOMY

CROSS-REFERENCE TO RELATED APPLICATIONS

This application claims priority to provisional patent application Ser. No. 62/463,137, filed Feb. 24, 2017 and titled GEARLESS MOTOR ASSEMBLY AND SYSTEM, the entire contents of which are incorporated herein by reference.

STATEMENT REGARDING FEDERALLY SPONSORED RESEARCH OR DEVELOPMENT

Not Applicable

INCORPORATION BY REFERENCE

All references, including but not limited to publications, patent applications and patents mentioned in this specification are hereby incorporated by reference to the same extent and with the same effect as if each reference was specifically and individually indicated to be incorporated by reference.

BACKGROUND OF THE INVENTION

Field of the Invention

The invention relates to systems, devices and methods for rotational medical devices. More specifically, but without limitation, gearless motor for use in rotational atherectomy procedures.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

High-speed rotational atherectomy devices may be used to clear the occlusions. In addition, thrombus or other soft tissue or plaque may require removal. A wide variety of other medical devices make use of prime movers, e.g., electric motors or pneumatics to generate a rotational output that is transferred to a drive shaft or other accessory attached operatively to the prime mover. Typical rotational systems comprise a prime mover with a prime mover gear that engages, e.g., a drive shaft gear to rotate the drive shaft itself.

Known, and exemplary, orbital atherectomy systems require a gear ratio, e.g., 4:1, to accommodate high revolutions per minute needed to achieve the treatment objectives of the drive shaft or other rotational accessory. The known geared design also allows the passage of a guidewire through the hypotube assembly. However, the addition of gears, e.g., a prime mover gear and a drive shaft (or rotational accessory) gear increases material and assembly cost, overall device weight and space requirements inside the handle housing the prime mover and interconnection with the rotational accessory. In addition, the gears also contribute to vibration and noise.

The present invention eliminates these gears for medical devices or other device and/or applications requiring a motor-driven rotational accessory.

DETAILED DESCRIPTION OF THE SEVERAL VIEWS OF THE DRAWINGS

Figure 1:
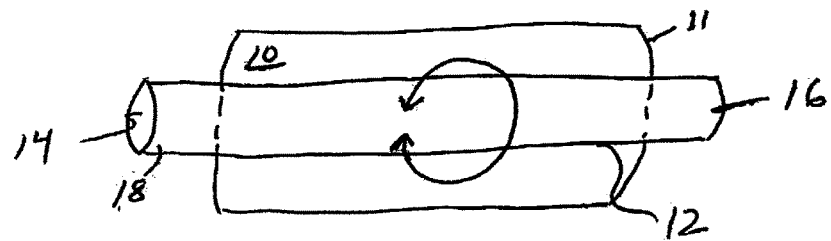
FIG. 1 illustrates a side cutaway view of one embodiment of the present invention.
Figure 2:
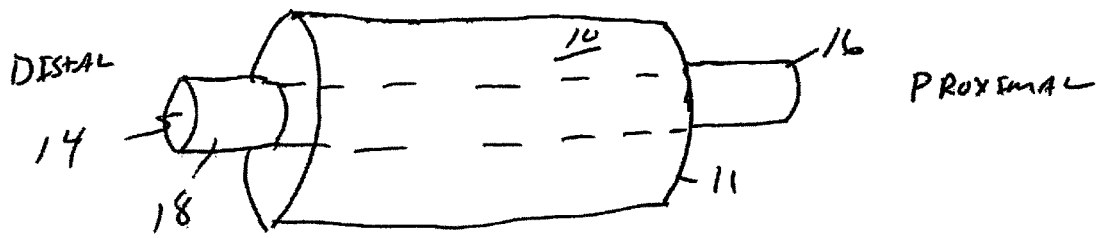
FIG. 2 illustrates a perspective view of one embodiment of the present invention.

FIGS. 1-5 illustrate one embodiment of a system comprising a gearless motor 10 with a housing 11, the gearless motor 10 adapted to rotate a rotational motor drive shaft 12 in a bi-directional manner. Such motors are sold by vendors such as Portescap.

The motor drive shaft 12 of the present invention extends through the gearless motor housing 11 as shown and further defines a motor drive shaft lumen 14 therethrough. Motor drive shaft 12 and motor drive shaft lumen 14 terminate proximally with a proximal end of the motor drive shaft 16 extending proximally from the gearless motor housing 11, and terminate distally with a distal end of the motor drive shaft 18 extending distally from the gearless motor housing 11. In certain embodiments, the proximal end 16 may not extend proximally away from gearless motor housing 11, with motor drive shaft 12 terminating proximally at a proximal end that is substantially coextensive with the proximal end of the gearless motor housing 11 in that case, while still allowing access to the motor drive shaft lumen 14 at the proximal end 16.

Figure 3:
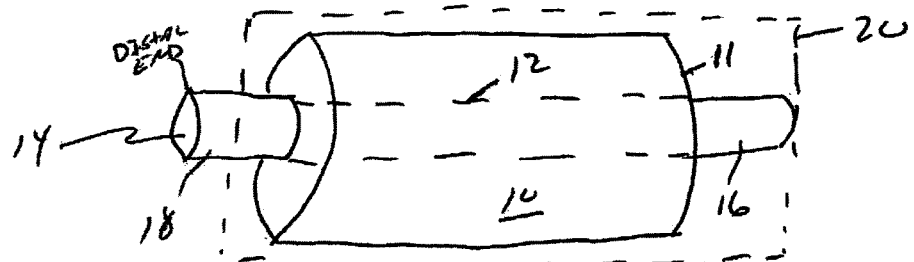
FIG. 3 illustrates a side perspective partial cutaway view of one embodiment of the present invention.
Figure 4:
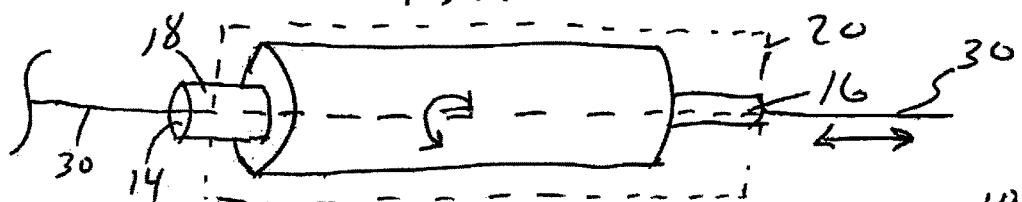
FIG. 4 illustrates a perspective partial cutaway view of one embodiment of the present invention.
Figure 5:
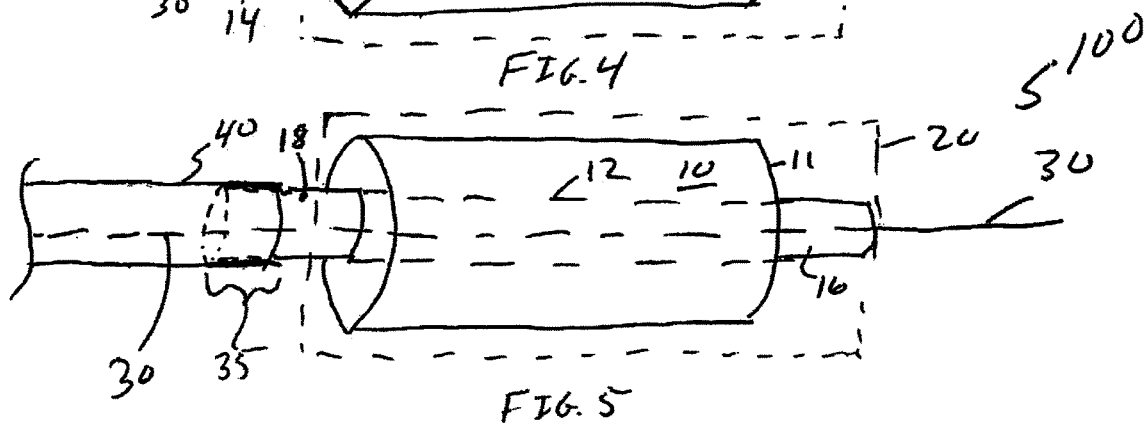
FIG. 5 illustrates a perspective partial cutaway view of one embodiment of the present invention.

A handheld device housing 20 as shown in dashed lines in FIGS. 3-5 may be provided to at least partially cover the gearless motor 10 and motor drive shaft 12 and drive shaft lumen 14 while allowing access to the motor drive shaft lumen 14 at the proximal end 16 of the motor drive shaft 12 and/or the distal end 18 of the motor drive shaft 12.

The gearless motor 10 may be an electric motor, may be brushless and may be gearless, and capable of bi-directional rotation at a range of rotational speeds, including greater or less than 20,000 rpm. The rotational speed settings for certain embodiments of the device may be fixed or may be controllable by the operator using known mechanisms. In all embodiments, the gearless motor 10 is adapted to rotate the motor drive shaft 12, including the proximal and distal ends 16, 18 thereof at a rotational speed that may be predetermined or that may be controllable using a speed controller and/or actuator that may be mounted on the device housing 20.

As shown in FIG. 3, a guidewire 30 may be translated through the motor drive shaft lumen 14, extending proximally away from the proximal end of the motor drive shaft 16 and distally away from the distal end of the motor drive shaft 18. Thus, the guidewire passes directly through the gearless motor via the motor drive shaft lumen 14 and may be translated axially and/or rotated by the operator to move the guidewire through a patient's tortuous vasculature to a site of interest, e.g., an occlusion requiring intervention. In certain embodiments, the guidewire 30 may enter and be positioned within the vasculature before translating the guidewire within the motor drive shaft lumen 14. In other embodiments, the guidewire 30 may be translated within the motor drive shaft lumen 14 before entry and positioning of guidewire 30 within the vasculature.

Figure 6:
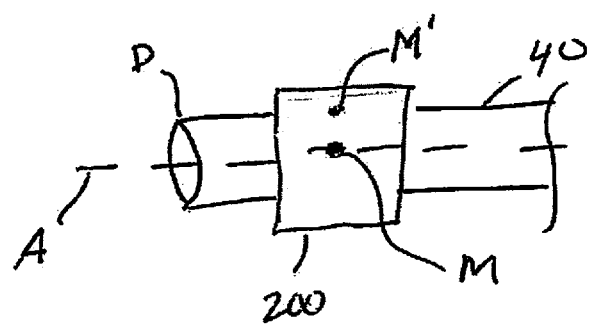
FIG. 6 illustrates a perspective cutaway view of one embodiment of the present invention.

Turning to FIGS. 4-6, the proximal and distal ends 16, 18 extend away proximally and distally, respectively, from the gearless motor housing 11. These extensions, particularly the distal extension, allows direct connection at connection region 35 with a torqueable flexible shaft 40, e.g., a hypotube or an interventional rotational drive shaft comprising a working element 200 on or near its distal end D as is well known in the art, for gearless rotation thereof. Exemplary working elements 200 may comprise, without limitation, one or more abrasive burrs, one or more abrasive crowns mounted on an elongate, flexible torqueable rotational drive shaft, an exemplary form of the torqueable flexible shaft 40, and as well known in the art, or one or more enlarged sections of the drive shaft, or a combination thereof. Further, the various forms of the working element 200 may comprise geometrically concentric or eccentric forms in relation to the rotational axis A of the drive shaft. Thus, the working element(s) 200 may be geometrically symmetrically arranged about the exemplary drive shaft or may be asymmetrically arranged about the drive shaft, or a combination thereof. Moreover, the working element(s) 200 may comprise a center of mass M that is located on the central rotational axis A of the drive shaft and/or may be located, as indicated by M', at a position that is radially offset from the rotational axis A of the exemplary drive shaft. Thus, in various configurations, the working element(s) 200 may induce a working diameter during high-speed rotation that is traced by the working elements wherein the traced working diameter is equal to or greater than the resting diameter of the working element(s) 200. In various configurations and combinations a system of working elements 200 may be provided that either tend to induce a larger working diameter compared with resting diameter, or tend to minimize the working diameter.

The connection mechanism between the torqueable flexible shaft 40 and the extending distal end 18 may be achieved by various means, including but not limited to friction fit, keyed fit, slotted fit, threaded engagement and equivalents and combinations thereof. In some embodiments, the connection region 35 may comprise a no-rotational-slip connection mechanism between the connected elements, while in other embodiments, the connection region 35 may be tuned to allow some rotational slip, while preventing axial or translational slipping, between the distal end 18 and the torqueable flexible drive shaft 40, at a predetermined torque threshold to prevent damage should, e.g., the working element of an interventional drive shaft become stuck within an occlusion, wherein the connection region 35 functions substantially as a clutch. In this regard, the connection region 35 may comprise a predetermined frictional coefficient that, when overcome by torque, allows a rotational slipping of the torqueable flexible shaft 40, relative to the motor drive shaft 12, to minimize damage to the patient if, for example, the working element of an exemplary interventional drive shaft has become stuck in an occlusion. Implementation of this configuration may comprise a friction fit which, in some embodiments may comprise magnetic materials used within the connection region 35 for both the distal end of the motor drive shaft 18 and the proximal end of the torqueable flexible shaft 40 in the connection region 35 wherein the magnetic force and/or static frictional forces created may be overcome by the torqueing shaft 40 at a maximum torqueing force threshold. Reaching this threshold thus allows the shaft 40 to rotate relative to motor drive shaft 12.

As shown in FIG. 5, the connection region 35 comprises a portion of the proximal end of the torque-able flexible shaft surrounding and engaging a portion of the outer surface of the distal end of the motor drive shaft 18. The skilled artisan will now readily recognize that the proximal end of the torqueable flexible shaft 40 may also fit within the lumen 14 of the distal end of the motor drive shaft 18 to comprise the connection region 35. Further, the proximal end of the torqueable flexible shaft 40 and the distal end of the motor drive shaft 18 may comprise a butted, end-to-end, connection region 35.

Thus, FIG. 5 illustrates one embodiment of an assembled system 100 comprising the gearless motor 10 with guidewire 30 positioned through the gearless motor drive shaft 12 and through the lumen of the interventional drive shaft 40, the interventional drive shaft 40 operationally engaged and attached to the distal end 14 of the motor drive shaft 12 for rotation of the interventional drive shaft 40.

Certain advantages of the gearless motor system 100 now become apparent. The guidewire 30 may be axially translated and/or rotated by the operator during the procedure and/or the gearless motor 10 and/or housing 20 may be axially translated along the guidewire 30 and/or rotated with respect to the guidewire 30. In addition, an operator may axially translate the torqueable flexible shaft 40, and therefore the working element attached to or near the distal end of the drive shaft 40, by simply translating the gearless motor 10 and housing 20 in a proximal or distal direction.

As partially described above, the various embodiments of the gearless motor provide at least the following advantages, compared with the typical two-gear motor-driven rotational systems:

Less cost;
Less components required;
Easier to assemble;
Less vibration;
Less noise;
Smaller overall design, particularly in the space required to house the gearless motor;
Less weight.

Moreover, we provide disclosure of the following patents and applications, each of which are assigned to Cardiovascular Systems, Inc., and incorporated herein in their entirety, each of which may comprise systems, methods and/or devices that is relevant to, or may be used with, various embodiments of the presently disclosed subject matter:

U.S. Pat. No. 9,468,457, "ATHERECTOMY DEVICE WITH ECCENTRIC CROWN";

U.S. Pat. No. 9,439,674, "ROTATIONAL ATHERECTOMY DEVICE WITH EXCHANGEABLE DRIVE SHAFT AND MESHING GEARS";

U.S. Pat. No. 9,220,529, "ROTATIONAL ATHERECTOMY DEVICE WITH ELECTRIC MOTOR";
U.S. Pat. No. 9,119,661, "ROTATIONAL ATHERECTOMY DEVICE WITH ELECTRIC MOTOR";
U.S. Pat. No. 9,119,660, "ROTATIONAL ATHERECTOMY DEVICE WITH ELECTRIC MOTOR";
U.S. Pat. No. 9,078,692, "ROTATIONAL ATHERECTOMY SYSTEM";
U.S. Pat. No. 6,295,712, "ROTATIONAL ATHERECTOMY DEVICE";
U.S. Pat. No. 6,494,890, "ECCENTRIC ROTATIONAL ATHERECTOMY DEVICE";
U.S. Pat. No. 6,132,444, "ECCENTRIC DRIVE SHAFT FOR ATHERECTOMY DEVICE AND METHOD FOR MANUFACTURE";
U.S. Pat. No. 6,638,288, "ECCENTRIC DRIVE SHAFT FOR ATHERECTOMY DEVICE AND METHOD FOR MANUFACTURE";
U.S. Pat. No. 5,314,438, "ABRASIVE DRIVE SHAFT DEVICE FOR ROTATIONAL ATHERECTOMY";
U.S. Pat. No. 6,217,595, "ROTATIONAL ATHERECTOMY DEVICE";
U.S. Pat. No. 5,554,163, "ATHERECTOMY DEVICE";
U.S. Pat. No. 7,507,245, "ROTATIONAL ANGIOPLASTY DEVICE WITH ABRASIVE CROWN";
U.S. Pat. No. 6,129,734, "ROTATIONAL ATHERECTOMY DEVICE WITH RADIALLY EXPANDABLE PRIME MOVER COUPLING";
U.S. patent application Ser. No. 11/761,128, "ECCENTRIC ABRADING HEAD FOR HIGH-SPEED ROTATIONAL ATHERECTOMY DEVICES";
U.S. patent application Ser. No. 11/767,725, "SYSTEM, APPARATUS AND METHOD FOR OPENING AN OCCLUDED LESION";
U.S. patent application Ser. No. 12/130,083, "ECCENTRIC ABRADING ELEMENT FOR HIGH-SPEED ROTATIONAL ATHERECTOMY DEVICES";
U.S. patent application Ser. No. 12/363,914, "MULTI-MATERIAL ABRADING HEAD FOR ATHERECTOMY DEVICES HAVING LATERALLY DISPLACED CENTER OF MASS";
U.S. patent application Ser. No. 12/578,222, "ROTATIONAL ATHERECTOMY DEVICE WITH PRE-CURVED DRIVE SHAFT";
U.S. patent application Ser. No. 12/130,024, "ECCENTRIC ABRADING AND CUTTING HEAD FOR HIGH-SPEED ROTATIONAL ATHERECTOMY DEVICES";
U.S. patent application Ser. No. 12/580,590, "ECCENTRIC ABRADING AND CUTTING HEAD FOR HIGH-SPEED ROTATIONAL ATHERECTOMY DEVICES";
U.S. patent application Ser. No. 29/298,320, "ROTATIONAL ATHERECTOMY ABRASIVE CROWN";
U.S. patent application Ser. No. 29/297,122, "ROTATIONAL ATHERECTOMY ABRASIVE CROWN";
U.S. patent application Ser. No. 12/466,130, "BIDIRECTIONAL EXPANDABLE HEAD FOR ROTATIONAL ATHERECTOMY DEVICE"; and
U.S. patent application Ser. No. 12/388,703, "ROTATIONAL ATHERECTOMY SEGMENTED ABRADING HEAD AND METHOD TO IMPROVE ABRADING EFFICIENCY".

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A rotational atherectomy system comprising:
   a gearless motor system comprising:
      a motor housing;
      a motor drive shaft that extends through the motor housing; and
      a gearless motor adapted to rotationally drive the motor drive shaft;
      the motor drive shaft comprising a distal end extending distally away from the motor housing of the gearless motor, a proximal end, and a motor drive shaft lumen defined by the motor drive shaft and extending therethrough,
      wherein the gearless motor comprises an actuator adapted to initiate and control the rotational speed of the motor drive shaft;
   a connection region wherein a proximal portion of a torqueable flexible shaft is directly connected with a distal portion of the motor drive shaft via a no-rotational-slip connection, the torqueable flexible shaft comprising a lumen therethrough, whereby the torqueable flexible shaft and the motor drive shaft are adapted to rotate at the same rotational speed at the connection region, and wherein the connection region is adapted to prevent the torqueable flexible shaft from axially translating relative to the motor drive shaft; and
   a guidewire adapted to translate and rotate within the motor drive shaft lumen and the torqueable flexible drive shaft lumen,
   wherein the motor housing and torqueable flexible drive shaft is configured to be translated proximally and distally over the guidewire;
   a device housing surrounding the motor housing and wherein the proximal end of the motor drive shaft terminates proximally from the motor housing of the gearless motor at a point that does not extend past the device housing;
   wherein the distal end of the motor drive shaft extends through, and terminates distally from, the device housing, and
   wherein the connection region between the proximal portion of the torqueable flexible shaft and the distal portion of the motor drive shaft is spaced distally away from the device housing,
   wherein the gearless motor, the motor drive shaft and the torqueable flexible shaft all rotate at substantially the same rotational speed.

2. The atherectomy system of claim 1, wherein the torqueable flexible shaft comprises a working element on or near a distal end of the torqueable flexible shaft.

3. The atherectomy system of claim 2, wherein the working element comprises at least one abrasive element.

4. The atherectomy system of claim 3, wherein the torqueable flexible shaft comprises an axis of rotation and wherein the at least one abrasive element comprises a center of mass located on the rotational axis of the torqueable flexible shaft.

5. The atherectomy system of claim 3, wherein the torqueable flexible shaft comprises an axis of rotation and wherein the at least one abrasive element comprises a center of mass located in a position that is radially offset from the rotational axis of the torqueable flexible shaft.

6. A gearless motor device for rotational atherectomy procedures comprising:
- a gearless motor system comprising:
  - a motor housing;
  - a motor drive shaft that extends through the motor housing, the motor drive shaft comprising a distal end extending distally away from the motor housing of the gearless motor, a proximal end extending proximally away from the motor housing of the gearless motor;
  - a motor drive shaft lumen defined by the motor drive shaft and extending therethrough; and
  - a gearless motor adapted to rotationally drive the motor drive shaft;
- a connection region wherein a proximal portion of a torqueable flexible shaft is directly connected with a distal portion of the motor drive shaft via a no-rotational slip connection, the torqueable flexible shaft comprising a lumen therethrough, whereby the torqueable flexible shaft and the motor drive shaft are adapted to rotate at the same rotational speed at the connection region, and wherein the connection region is adapted to prevent the torqueable flexible shaft from axially translating relative to the motor drive shaft; and
- a device housing surrounding the motor housing, and wherein the proximal end of the motor drive shaft terminates proximally from the motor housing of the gearless motor at a point that does not extend past the device housing,
- wherein the distal end of the motor drive shaft extends through, and terminates distally from, the device housing, and
- wherein the connection region between the proximal portion of the torqueable flexible shaft and the distal portion of the motor drive shaft is spaced distally away from the device housing,
- wherein the gearless motor, the motor drive shaft and the torqueable flexible shaft all rotate at substantially the same rotational speed.

* * * * *